US010348479B2

(12) United States Patent
Tebbe et al.

(10) Patent No.: US 10,348,479 B2
(45) Date of Patent: Jul. 9, 2019

(54) SIGNAL DETECTION FOR OPTICAL COMMUNICATION NETWORK

(71) Applicant: Alcatel-Lucent USA Inc., Murray Hill, NJ (US)

(72) Inventors: Roy B. Tebbe, Raleigh, NC (US); Kaleb Droskiewicz, Raleigh, NC (US)

(73) Assignee: NOKIA OF AMERICA CORPORATION, Murray Hill, NJ (US)

( * ) Notice: Subject to any disclaimer, the term of this patent is extended or adjusted under 35 U.S.C. 154(b) by 0 days.

(21) Appl. No.: 15/606,094

(22) Filed: May 26, 2017

(65) Prior Publication Data

US 2018/0183443 A1 Jun. 28, 2018

Related U.S. Application Data

(60) Provisional application No. 62/439,687, filed on Dec. 28, 2016.

(51) Int. Cl.
| *H04L 7/00* | (2006.01) |
| *H04L 7/10* | (2006.01) |
| *H04B 10/00* | (2013.01) |
| *H04B 10/40* | (2013.01) |
| *H04B 10/50* | (2013.01) |
| *H04B 10/60* | (2013.01) |
| *H04Q 11/00* | (2006.01) |
| *H04B 10/272* | (2013.01) |

(52) U.S. Cl.
CPC .......... *H04L 7/0075* (2013.01); *H04B 10/00* (2013.01); *H04L 7/10* (2013.01); *H04Q 11/0001* (2013.01); *H04B 10/272* (2013.01); *H04B 10/40* (2013.01); *H04B 10/50* (2013.01); *H04B 10/60* (2013.01)

(58) Field of Classification Search
None
See application file for complete search history.

(56) References Cited

U.S. PATENT DOCUMENTS

| 7,583,898 B1 | 9/2009 | Dalton et al. | |
| 8,538,258 B2 | 9/2013 | Suvakovic | |
| 2005/0019036 A1* | 1/2005 | Soto | H04J 398/135 14/2 |
| 2010/0221000 A1* | 9/2010 | Yang | H04B 10/03 398/38 |
| 2011/0013904 A1* | 1/2011 | Khermosh | G01M 11/3118 398/16 |

\* cited by examiner

*Primary Examiner* — Darren E Wolf
(74) *Attorney, Agent, or Firm* — Harness, Dickey & Pierce, P.L.C.

(57) ABSTRACT

In at least some example embodiments an optical line terminal (OLT) may include processing circuitry configured to, convert an optical signal received from an optical network terminal (ONT) to a digital signal; and monitor the digital signal for a convergence event, the digital signal representing an optical signal received from the ONT and the convergence event being an event associated with the ONT.

17 Claims, 6 Drawing Sheets

FIG. 6

| Preamble: | Delimiter: | Header information: | Payload data: | Trailer: |
|---|---|---|---|---|
| Typically a binary 1010 pattern | Marker to indicate start of packet data | May contain management information for packet | May include actual data and/or error correction data | Data parity information |

SIGNAL DETECTION FOR OPTICAL COMMUNICATION NETWORK

This application is a non-provisional application that claims priority under 35 U.S.C. § 119 to U.S. provisional App. No. 62/439,687, filed on Dec. 28, 2016, the entire content of which is hereby incorporated by reference in its entirety.

BACKGROUND

1. Field

Example embodiments relate generally to an apparatus configured to perform signal detection for an optical communication network, a method or a non-transitory computer readable medium configured to perform same. For example, at least some example embodiments relate to an apparatus configured to improve detection of an upstream signal transmission in an optical communication network, a method or a non-transitory computer readable medium configured to perform same.

2. Related Art

Digital telecommunications networks (i.e., networks that facilitate the communication of data, voice, video, etc., between parties or between an exchange and a subscriber) may include active components, such as repeaters, relays and other such devices that consume power, in a path therebetween. In addition to using power, the active components may be subject to failure and performance degradation over time, and may need periodic maintenance.

Passive optical networks (PONS), which may include optical fiber and passive components rather than active components in the path, have been developed to reduce (or, alternatively, eliminate) at least some of the aforementioned problems. In a PON, a single optical fiber can run from the exchange to a passive splitter located near a group of subscribers, such as a neighborhood or office complex, and individual optical fibers can run from the splitter to individual subscribers in the group or to sub-groups of the group.

A PON may include an optical line terminator (OLT) at the exchange and a number of optical network units (ONUs), also known as optical network terminals (ONTs), located at or near the subscriber's premises (e.g., home, office building, etc.), with optical fiber and splitters between the OLT and ONUs.

During operation of the PON, a continuous data stream may be transmitted downstream from the OLT to various ones of the ONUs, or transmitted upstream as bursts of data from various ones of the ONUs to the OLT. The OLT may use a signal detect (SD) indicator to indicate the beginning of an upstream burst, and begin a process to synchronize the OLT clock to the upstream burst in order to properly recover the upstream bursts of data.

Conventionally, an optics module associated with the OLT may generate the SD indicator when the averaged analog power level of an upstream burst crosses a threshold setting. For example, the optics module may include a limiting amplifier (LA) that monitors the upstream optical signal to detect a fixed edge rate pattern. The optics module may output (or, alternatively assert) the SD indicator detector via a dedicated signal detect (SD) pin to indicate the presence or absence of an upstream burst. The limiting amplifier (LA) may monitor for a fixed edge rate pattern in the upstream optical signal to detect the beginning of an upstream burst. The SD indicator may be a positively asserted indicator indicating the presence of the upstream burst. Alternatively, the SD indicator may be a loss of signal (LOS) indicator that is de-asserted when an upstream burst is present, where the LOS indicator may be considered as an inverted SD indicator.

In addition to a dedicated interface pin between the optics module and digital processing circuitry in the OLT 100, the optics module may output the SD indicator within a fixed time interval dictated by several factors including, for example, noise filtering (e.g., to prevent false detection) and a time delay associated with circuitry that generates the SD indicator. As data rates increase, bits in the upstream burst may be output in a shorter length of time, however, a conventional OLT may not be scalable with faster data rates because, for example, the LA may be limited to monitoring for a fixed pattern as well as limited to waiting until the individual edges of the optical signal are detected.

Therefore, as data rates increase, a conventional OLT may require a longer upstream burst to properly detect the same.

SUMMARY

In one or more example embodiments, an OLT may perform a virtual signal detect based on the upstream digital data itself to detect the preamble, rather than based on analyzing an analog power level of either the optical signal or the electrical signal. By analyzing the upstream digital data itself, the OLT may detect the upstream burst in a fraction of the time required by a conventional optics module. Therefore, since the OLT may detect the preamble faster, the OLT may be scalable to increased data rates or allow for a shorter preamble to be utilized, thus increasing the line bandwidth utilization. Further, the OLT may not need a dedicated SD pin on the optics module, thus, freeing this pin on the connector interface for alternative functions.

At least some example embodiments relate to an optical line terminal (OLT).

In some example embodiments, the OLT includes processing circuitry configured to monitor a digital signal for a convergence event, the digital signal representing an optical signal received from an optical network terminal (ONT), the convergence event being an event associated with the ONT.

In some example embodiments, the processing circuitry includes a clock data recover (CDR) circuit configured to perform a lock operation to align a phase of the digital signal with a reference clock associated with the OLT, and a virtual signal detector configured to detect the convergence event prior to completion of the lock operation.

In some example embodiments, the OLT further includes an optical module configured to, receive the optical signal, the optical module including at least an optical receiver having a detection threshold associated therewith, the OLT configured to adjust, during a settling time, the detection threshold based on the optical signal, and wherein the processing circuitry is configured to detect the convergence event prior to an expiration of the settling time.

In some example embodiments, the processing circuitry is configured to monitor the digital signal in one of discrete chunks of data and a moving average of the data.

In some example embodiments, the discrete chucks of data are each 32 bits.

In some example embodiments, the processing circuitry further includes a serial deserializer configured to convert the data within the digital signal from serial data to parallel data.

In some example embodiments, the processing circuitry is configured to monitor the digital signal for the convergence event by one of (i) detecting a level of randomness in the digital signal and (ii) detecting a level of disparity of the digital signal.

In some example embodiments, the processing circuitry is configured to detect the convergence event based on the digital signal and a threshold, the threshold being associated with a change in one of the level of randomness and the level of disparity of the digital signal.

In some example embodiments, the processing circuitry is configured to one of (i) separate random intra-burst data from signal data and (ii) detect whether the ONT is rouge based on detection of the convergence event.

In some example embodiments, the signal data is a preamble of an upstream burst from the ONT.

At least some other example embodiments relate to a method of operating an optical line terminal (OLT).

In some example embodiments, the method includes monitoring a digital signal for a convergence event, the digital signal representing an optical signal received from an optical network terminal (ONT), the convergence event being an event associated with the ONT.

In some example embodiments, the monitoring includes performing, via a clock data recover (CDR) circuit, a lock operation to align a phase of the digital signal with a reference clock associated with the OLT, and detecting, via a virtual signal detector, the convergence event prior to completion of the lock operation.

In some example embodiments, the method further includes receiving, via an optical module, the optical signal, the optical module including at least an optical receiver having a detection threshold associated therewith, the OLT configured to adjust, during a settling time, the detection threshold based on the optical signal, and wherein the monitoring detects the convergence event prior to an expiration of the settling time.

In some example embodiments, the monitoring monitors the digital signal in one of discrete chunks of data and a moving average of the data.

In some example embodiments, the monitoring monitors the digital signal for the convergence event by detecting one of (i) a level of randomness in the digital signal and (ii) a level of disparity of the digital signal.

In some example embodiments, the monitoring detects the convergence event based on the digital signal and a threshold, the threshold being associated with a change in one of the level of randomness and the level of disparity of the digital signal.

At least some other example embodiments relate to a non-transitory computer readable medium.

In some example embodiments, the non-transitory computer readable medium stores instructions that, when executed by processing circuitry associated with an optical line terminal (OLT), configures the processing circuitry to monitor a digital signal for a convergence event, the digital signal representing an optical signal received from an optical network terminal (ONT), the convergence event being an event associated with the ONT.

In some example embodiments, the instructions, when executed, configure the processing circuitry to, perform, via a clock data recover (CDR) circuit, a lock operation to align a phase of the digital signal with a reference clock associated with the OLT, and detect, via a virtual signal detector, the convergence event prior to completion of the lock operation.

In some example embodiments, the instructions, when executed, configure the processing circuitry to, receive, via an optical module, the optical signal, the optical module including at least an optical receiver having a detection threshold associated therewith, the OLT configured to adjust, during a settling time, the detection threshold based on the optical signal, and wherein the processing circuitry is configured to detect the convergence event prior to an expiration of the settling time.

In some example embodiments, the instructions, when executed, configure the processing circuitry to monitor the digital signal for the convergence event by detecting one of (i) a level of randomness in the digital signal and (ii) a level of disparity of the digital signal.

BRIEF DESCRIPTION OF THE DRAWINGS

At least some example embodiments will become more fully understood from the detailed description provided below and the accompanying drawings, wherein like elements are represented by like reference numerals, which are given by way of illustration only and thus are not limiting of example embodiments and wherein:

FIG. 6. Illustrates an example of an upstream data stream according to some example embodiments.

DETAILED DESCRIPTION

Figure 1:
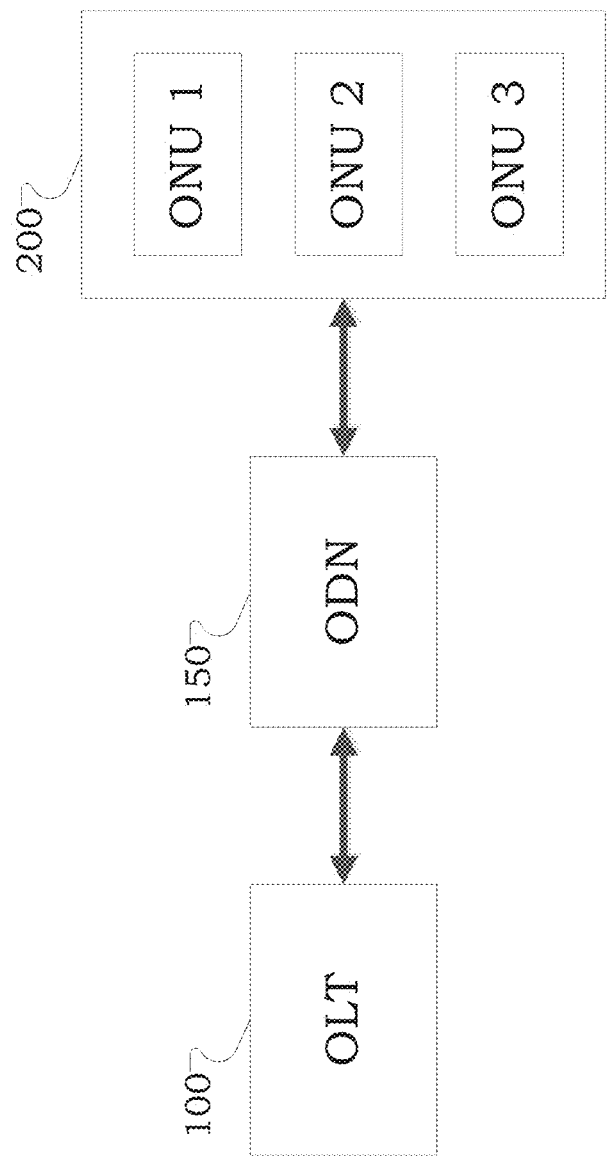
FIG. 1 illustrates a passive optical network (PON) according to at least some example embodiments.

Various example embodiments will now be described more fully with reference to the accompanying drawings in which some example embodiments are shown.

Detailed illustrative example embodiments are disclosed herein. However, specific structural and functional details disclosed herein are merely representative for purposes of describing at least some example embodiments. Example embodiments may, however, be embodied in many alternate forms and should riot be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but on the contrary, example embodiments are to cover all modifications, equivalents, and alternatives falling within the scope of example embodiments. Like numbers refer to like elements throughout the description of the figures. As used herein, the term "or" includes any and all combinations of one or more of the associated listed items.

FIG. 1 illustrates a passive optical network (PON) according to at least some example embodiments.

Referring to FIG. 1, a PON may include an optical line terminator (OLT) 100 and a plurality of optical network units (ONUs) 200, also known as optical network terminals (ONTs).

The OLT 100 may reside at an exchange, and the ONUS 200 may reside at or near a subscriber's premises (e.g., home, office building, etc.) The OLT 100 may be connected to the ONUs 200 via an optical distribution network (ODN) 150.

The ODN 150 may include components for supporting optical data transmission including fiber optic connectors, optical fibers, and passive optical splitters. Further, in accordance with known structures of ODNs, the ODN 150 may include, for example, feeder fiber, distribution fiber, drop fiber, at least one optical distribution point, or at least one optical access point. While a particular PON topoloy is illustrated in FIG. 1, example embodiments are not limited thereto. For example, the PON may have any suitable topology with a various number of ONUs, splitters, fibers, etc.

The OLT 100 may exchange data with the ONUs 200 using various standards promulgated by, for example, the International Telecommunications Union (ITU) and the Institute of Electrical and Electronics Engineers (IEEE), which have adopted recommendations of the Full Service Access Networks (FSAN) organization, including G983.x, sometimes referred to as "broadband PON" (BPON), G984.x, sometimes referred to as "gigabit PON" (GPON), G.987.x (XGPON) and G.989.X (NGPON2).

The OLT 100 may transmit optical signals downstream to the ONUs 200 via the ODN 150 using, for example, lasers included in the OLT 100, and may receive optical signals transmitted upstream from the ONUs 200 via the ODN 150.

The ONUs 200 may convert the downstream optical signals received from the OLT 100 into electrical signals and transmit the electrical signals to end-user devices or convert electrical signals from the end-user devices into optical signals and transmit the optical signals to the OLT 100 via the ODN 120 using, for example, lasers included in the ONUs 200.

In the downstream direction, i.e., data transmitted from the exchange to one of the subscribers, the data packets (also referred to as cells) may be broadcast from the OLT 100 to all of the ONUs 200 in the network, and one of the ONUs 200 that is associated with the subscriber can receive the data by matching an address embedded in the data to an address associated with the ONU 200. Since the OLT 100 may be the only device transmitting data in the downstream direction, the downstream data may not experience collisions with data destined for other ONUs 200.

However, in the upstream direction, i.e., data transmitted from one of the subscribers to the exchange, data packets transmitted from the subscriber may experience packet collisions, if two or more ONTs 200 are transmitting upstream data simultaneously to the OLT 100. In order to reduce the probability of (or, alternatively, prevent) these packet collisions, the ONTS 200 may use PON burst-mode technology to burst the data packets upstream at relatively high bit rates by utilizing time-division multiple access (TDMA) to multiplex the data packets with data transmitted from other ONTs 200 and therefore other subscribers.

Differences in the amplitude of upstream signals from the ONUs 200 may vary from ONU 200 to ONU 200 for a number of reasons, including, for example, differences in the number of splits in the paths between various ones of the ONUs 200 and the OLT 100 and different distances from the ONUs 200 to the OLT 100. Further, individual upstream bursts may require varying amounts of amplification due to the differences in their respective optical power level.

To cope with these differences, the OLT 100 may perform automatic gain controller (AGC) to adjust the amplification level based on differences in the power level between successive bursts, where the time required to perform AGC may be referred to as a settling time. The OLT 100 may reduce the settling time by activating an optics reset signal once a positive indication of an upstream burst has been received, to reduce the amount of time before the AGC is performed.

As discussed in more detail below with reference to FIGS. 2-6, in order to reduce the time taken by the OLT 100 to detect the beginning of an upstream burst, rather than directly monitoring the optical signal power level using an optics module to detect the upstream burst, in one or more example embodiments, the OLT 100 may perform a virtual signal detect to detect the upstream burst by monitoring the digital data received from the optics module using a digital logic chip.

Figure 2:
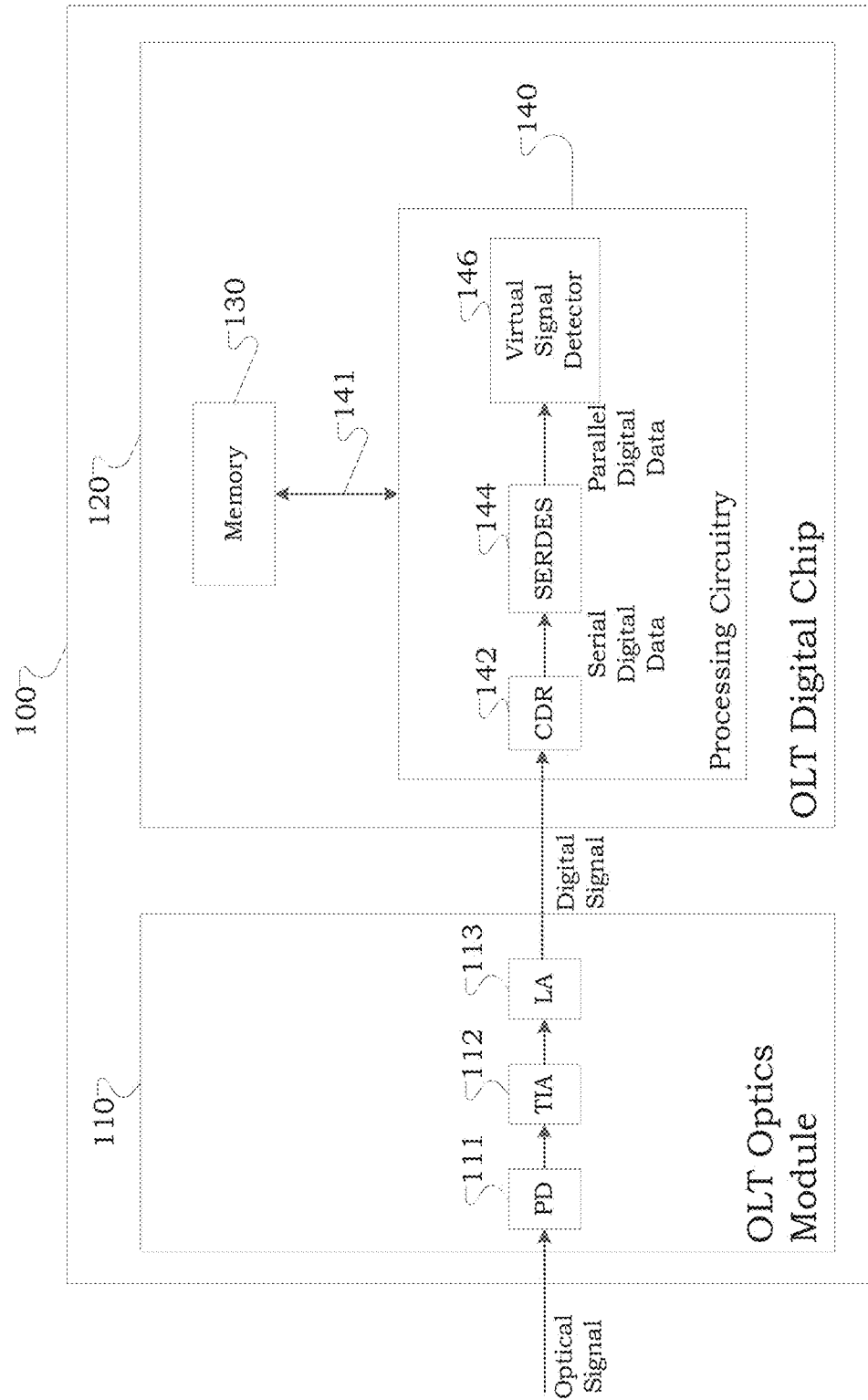
FIG. 2 illustrates an optical line terminal (OLT) included in a PON according to at least some example embodiments.

FIG. 2 illustrates an optical line terminal (OLT) according to at least some example embodiments.

Referring to FIG. 2, the OLT 100 may include an OLT optics module 110 and an OLT digital chip 120.

The OLT optics module 1110 may include a photo detector (PD) 111, a trans-impedance amplifier (TIA) 112, and a limiting amplifier (LA) 113.

The photo detector 111 may convert the received optical signal into an electrical signal, the trans-impedance amplifier 112 and the limiting amplifier 113 may restore the electrical signal to a digital signal.

The OLT digital chip 120 may include a memory 130 and processing circuitry 140, which may be connected via a bus 141.

The memory 130 may be a non-transitory computer readable storage medium that generally includes a random access memory (RAM), read only memory (ROM), or a permanent mass storage device, such as a disk drive. The memory 130 may also store an operating system and any other routines/modules/applications for providing the functionalities of the OLT digital chip 120. These software components may also be loaded from a separate computer readable storage medium into the memory 130 using a drive mechanism (not shown). Such separate computer readable storage medium may include a disc, tape, DVD/CD-ROM drive, memory card, or other like computer readable storage medium (not shown). In some example embodiments, software components may be loaded into the memory 140 via one or more interfaces (not shown), rather than via a computer readable storage medium.

The processing circuitry 140 may be, but not limited to, a processor, Central Processing Unit (CPU), a controller, an arithmetic logic unit (ALU), a digital signal processor, a microcomputer, a field programmable gate array (FPGA), an Application Specific Integrated Circuit (ASIC), a System-on-Chip (SoC), programmable logic unit, a microprocessor, or any other device capable of performing operations in a defined manner.

The processing circuitry 140 may be configured, through a layout design or execution of computer readable instructions stored in the memory 130, as a special purpose computer to perform the functions of a clock data recovery (CDR) circuit 142, a Serializer/Deserializer (SERDES) 144 and a virtual signal detector 146.

The CDR 142 may extract the received data from the data signal. The CDR 142 may align the phase (location edges for transitions from logic "1" to logic "0" or logic "0" to logic "1") of the incoming data with an internal reference clock to generate parallel digital data. The time taken for the CDR 142 to align the reference clock with the incoming data may be referred to as a CDR lock time. The OLT 100 may properly receive data once the CDR 142 is locked.

The OLT digital chip 120 may receive high speed digital data from the optics module 110 in serial form such that the logical bits are sent one after the other. The SERDES 144 may convert the serial digital data to parallel digital data by, for example, grouping the serial data in 32 bit groups, and transmitting the group of data to the virtual signal detector 146 over a 32 bit wide bus. However, example embodiments are not limited thereto.

Conventionally, the optics module 110 itself may detect the upstream burst, and may inform a digital logic chip of receipt of the upstream burst via a dedicated signal detect (SD) pin (not shown) between the optics module 110 and the digital logic chip. For example, conventionally, the limiting amplifier 113 associated with the optics module 110 may have a detection threshold (known as a slicing level) for a logic '1' or logic '0' bit. Bit errors may occur if the amplification of the optics module 110 is too high or too low to detect the bits of a packet. During the settling time, which may occur at the beginning of an upstream burst packet, the received data may be interpreted as all logical '0' (amplification too low) or all logical '1' (amplification too high). The limiting amplifier 113 may perform the automatic gain controller (AGC) to adjust the detection threshold until the detection threshold is centered between the logic "1" level and the logic "0" level of the upstream packet in order to receive data bits properly.

The beginning of an upstream burst may contain a logical '1010' pattern as shown in FIG. 6 to allow the optics module 110 to perform the AGC. This pattern, referred to as a preamble, may be sufficiently long to allow the settling time to complete, allow the optics module 110 to detect the average power of the upstream burst, and alert the OLT 120, via the optics reset signal, before the start of the payload data.

However, since the upstream burst preamble does not carry subscriber data, it may be desirable to shorten the preamble to increase (or, alternatively, maximize) the available bandwidth for subscriber payload data. Further, the optics module 110 may not be scalable with increasing data rates, and, therefore, conventionally, it may be difficult to shorten the preamble and still provide sufficient time for the optics module 110 to detect the preamble.

In contrast to the aforementioned optical burst detection, in one or more example embodiments, the our digital chip 120 may monitor the upstream digital signal for a change in the digital content of the upstream digital signal. For example, the virtual signal detector 146 may detect the preamble by detecting a convergence event in the upstream digital signal (rather than analyzing the optical signal directly). In some example embodiments, the convergence event may be a rapid change in disparity. In other example embodiments, convergence event may be a desired level of randomness in the incoming digital data. The convergence event will be discussed below in more detail with regard to FIGS. 4 and 5.

By monitoring the digital signal directly, the time required by the optics module 110 may be reduced (or, alternatively, eliminated). Further, the OLT digital chip 120 may include circuitry having a relatively higher processing speed than a conventional signal detect SD performed by the optics module 110. Further, while the conventional SD may not be scalable with increasing data rates, the OLT 120 digital detection circuitry is scalable in order to receive high speed payload data. The use of high speed circuitry that scales with data rate allows for a significantly faster detection of upstream burst, and thereby allows for shorter preambles and increased bandwidth utilization. Further, since the OLT digital chip 120 detects the upstream burst itself, in one or more example embodiments, the OLT 100 may eliminate the dedicated signal detect interface pin between the optics module 110 and OLT digital chip 120.

As will be appreciated, depending on implementation, the OLT 100 may include additional components other than those shown in FIG. 2. However, it is not necessary that all of these components be shown in order to convey illustrative example embodiments to persons having ordinary skill in the art.

Figure 3:
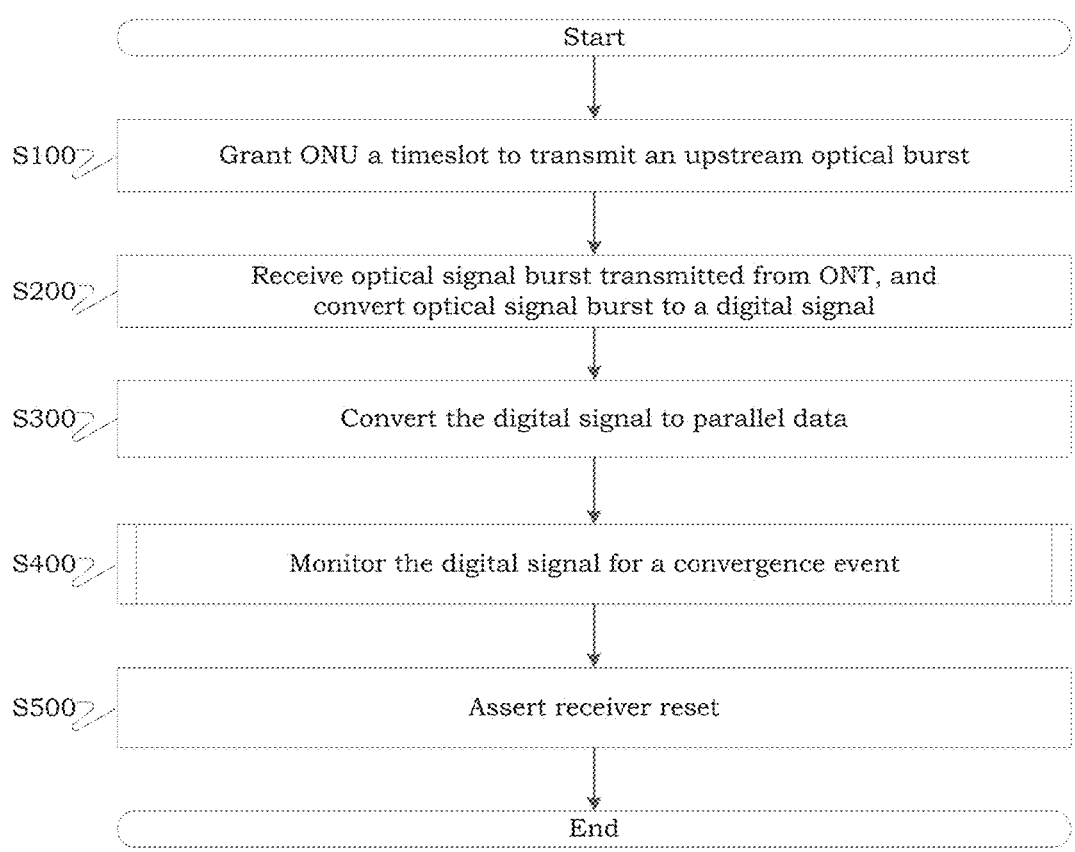
FIG. 3 illustrates a method of detecting an upstream optical burst according to at least some example embodiments.

FIG. 3 illustrates a method of detecting an upstream optical burst according to at least some example embodiments.

Referring to FIGS. 1-3, in operation S100, the OLT 100 may grant a timeslot to a particular one of the ONUs 200 to allow the ONU 200 to transmit upstream data during an upstream optical burst.

For example, the OLT 100 may regularly transmit a bandwidth map downstream to the ONUs 200. The bandwidth map may contain start time and burst length information for the ONUs 200 to utilize to transmit the upstream optical burst.

In operation S200, the OLT 100 may receive the optical burst from one of the ONUs 200. For example, the OLT optics module 110 may receive the optical burst after a delay caused by, for example, a distance between the OLT 100 and the ONU 200, and the OLT optics module 110 may perform optical to electrical conversion and output the burst of the digital signal to the OLT digital chip 120.

In operation S300, the OLT 100 may convert the digital signal to parallel data. For example, the clock data recovery (CDR) 142 may perform a clock data recovery on the incoming data to generate parallel digital data, and the Serializer/Deserializer (SERDES) 144 may perform a serial to parallel conversion on the digital signal in order to align a local reference clock of the OLT 100 with a phase and frequency of the digital signal.

In operation S400, as discussed in more detail below with reference to FIGS. 4 and 5, the OLT 100 may monitor the received data for the convergence event.

For example, conventionally, data received before the CDR locks may be discarded. However, in one or more example embodiments, the OLT 100 may use this pre-lock data to perform virtual signal detect by detecting the convergence event within a small fraction of the length of the preamble. In contrast, a typical optical signal detect assertion may be delayed for several multiples of the preamble length during the settling time for gains of an amplifier, such as the trans-impedance amplifier (TIA) 112 and limiting amplifier (LA) 113, to properly adjust to the incoming burst.

In operation S500, the OLT 100 may selectively assert various receiver resets in response to the OLT detecting the convergence event.

For example, the OLT 100 may assert an optical reset to center elements of the OLT optics module 110, such as the TIA 112 and the LA 113, to reduce the settling time associated with reception of the burst data. The OLT 100 may also assert a reset for data buffers in the CDR 142 and the SERDES 144 to remove any corrupted or unusable data to allow for proper reception of upstream burst payload data.

Figure 4:
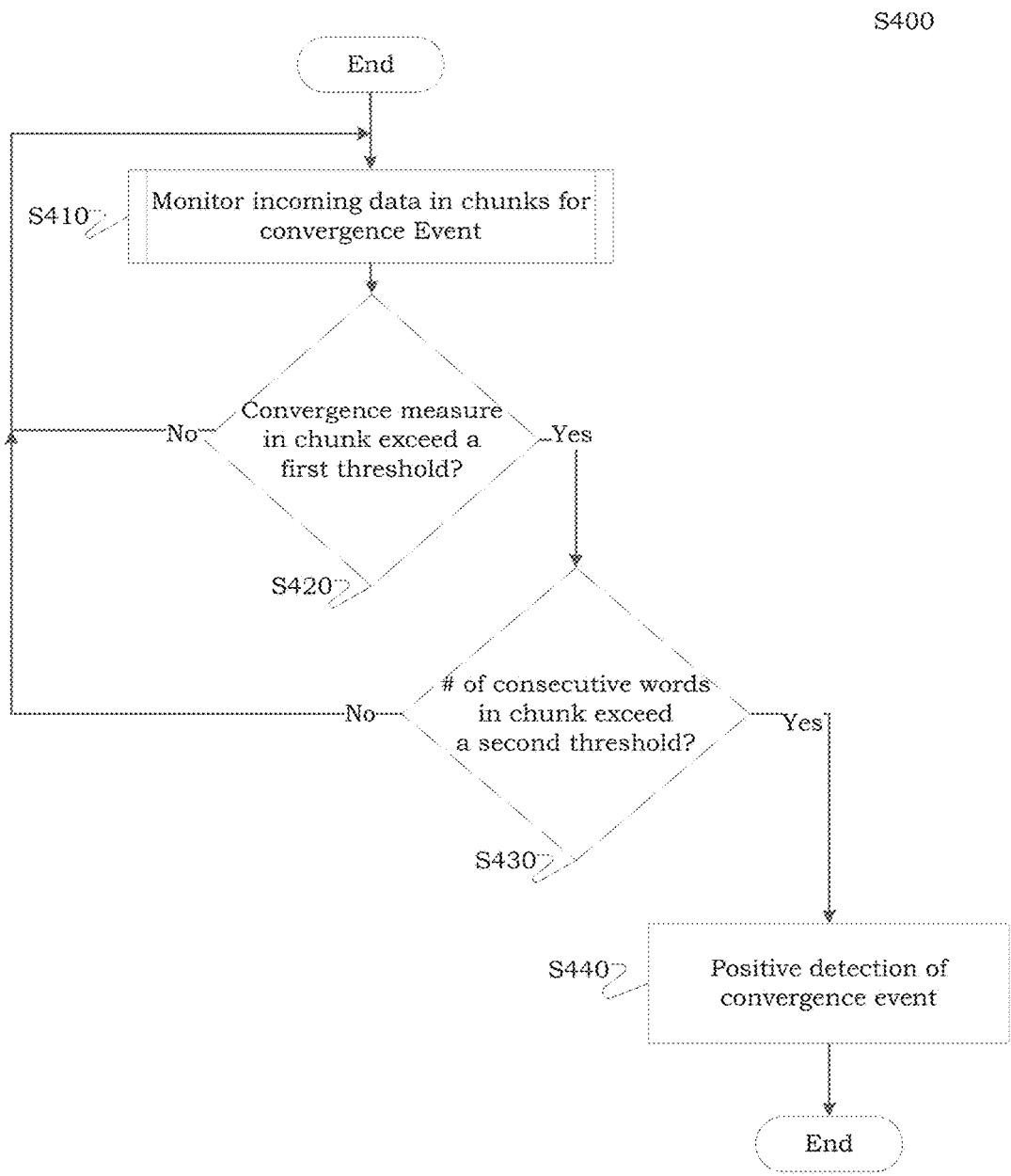
FIG. 4 illustrates a method of monitoring parallel data for a convergence event according to at least some example embodiments.

FIG. 4 illustrates a method of monitoring parallel data for a convergence event according to at least some example embodiments.

Referring to FIGS. 1-4, in operation S410, as discussed in more detail below with reference to FIG. 5, the OLT 100 may monitor incoming data in chunks for a convergence event. For example, the OLT digital chip 120 may monitor the parallel data in increments of 32 bits (e.g., a word) to detect the presence of the convergence event.

Figure 5:
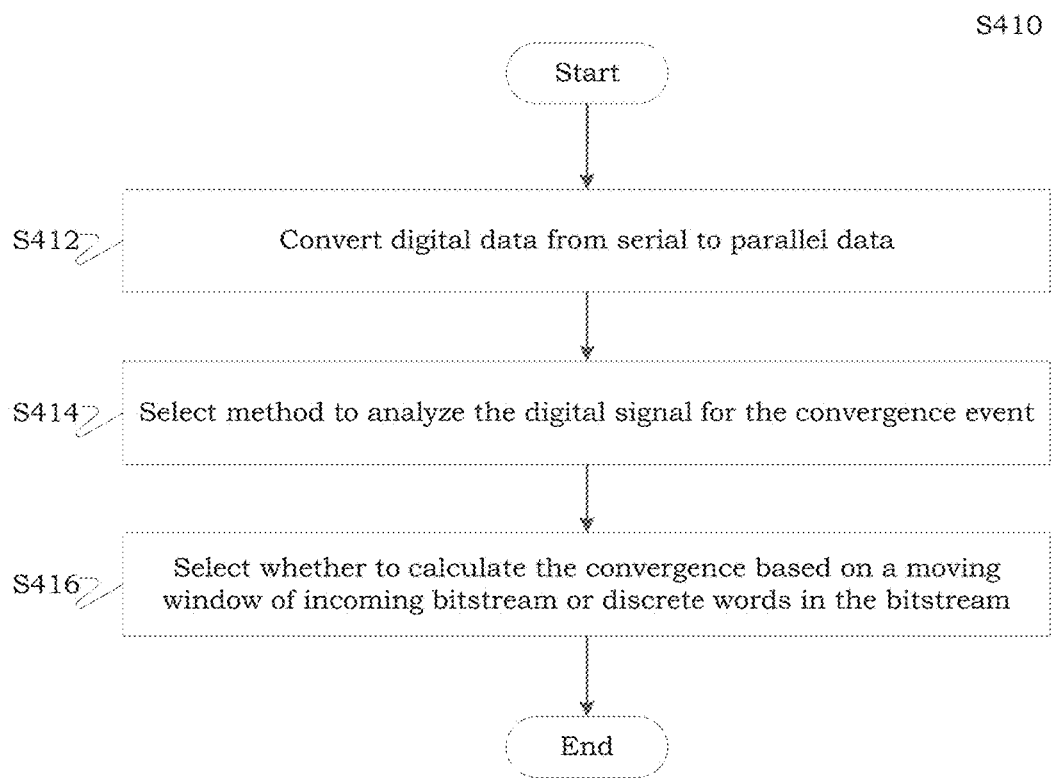
FIG. 5 illustrates a method of monitoring parallel data to determine a measure of disparity according to at least some example embodiments.

FIG. 5 illustrates a method of monitoring parallel data to determine a measure of convergence according to at least some example embodiments.

Referring to FIGS. 1-5, in operation S412, the OLT 100 may convert the digital data from serial data to parallel data. For example, the OLT 100 may convert the digital data in chunks of 32 bit words.

In operation S414, the OLT 100 may select a method to analyze the digital signal for the convergence event. For example, the OLT 100 may determine whether to analyze the randomness R of the signal or calculate the signal disparity d.

For example, intra-burst data between data bursts may appear as random noise to the OLT 100. In contrast, a data burst may be less random. Therefore, in some example embodiments, the OLT 100 may analyze the level of randomness R of a burst to determine whether the burst is random inter-burst noise or a data burst. The OLT 100 may utilize Equation 1, discussed below, to determine the level of randomness R, however, example embodiments are not limited thereto:

$$R = x_{1\text{-}32} \, \& \, INV(x_{3\text{-}34}) \qquad \text{Eq. 1}$$

In Equation 1, R may represent the randomness of a signal X, X may represent the signal, and the subscripts of X may represent the individual bits of the signal. The operator "&" may denote a logical AND operation, such that 1 & 1=1, all other combinations equal 0. The operator INV may denote the bitwise inverse, such that if x=1010, then INV(x)=0101. As can be seen the logical AND of x and inv(x) may be 0.

When a delayed version, delayed in multiples of 2 bits, of the preamble is compared to itself the result will also be 0. Random noise will likely not align with its inverse, and, therefore a much larger number will likely result. However, the aforementioned computation may be complex. Typically, the early burst data presents itself to the OLT digital chip 120 as high 1's content data.

Therefore, in some other example embodiments, the OLT 100 may utilize a less computationally complex algorithm based on signal disparity d. For example, the OLT 100 may utilize Equation 2 to sum the logic '1' or logic '0' content over the length, n of the data chunk being tested (typically n=32).

$$d = \sum_{i=1}^{n} x_i \qquad \text{Eq. 2}$$

In Equation 2, d may represent the calculated value of disparity, $x_i$ may represent the individual bits of the 32 bit chunk of data, i.e., $x_{10}$ may represent the $10^{th}$ bit in the 32 bit word.

By computing the value for R or d, the OLT 100 may set a threshold $T_\theta > z$ such that the signal convergence above the threshold indicates burst arrival. The value of z is empirically determined and is programmable. The OLT 100 may set separate thresholds for the randomness R and disparity d (logic level low (0) and logic level high (1)). The thresholds may be set based on an empirical study.

In operation S416, the OLT 100 may select whether to calculate the convergence based on discrete chunks of data (e.g., 32 bit data) or based on a running total. For example, if the serial stream is 128 bits long, the discrete chunks may be bits 0-31, bits 32-63, bits 64-95, and bits 96-127. Alternatively, the OLT 100 may calculate the convergence based on a running total, for example, based on bits 0-31, bits 1-32, bits 2-33, etc. The OLT 100 may utilize a configurable (or, alternatively, a pre-configured) step size in the above calculation.

As discussed below, the OLT 100 may utilize the convergence to determine whether the measured signal contains noise or whether the measured signal is the beginning of an upstream burst, such as a preamble from one of the ONUs 200.

Referring back to FIG. 4, in operation S420, the OLT 100 may determine whether the convergence of a particular digital value in the chunk exceeds a first threshold. The first threshold may be empirically determined. For example, the first threshold may be calculated based on characterization of the intra-burst data to reduce (or, alternatively, minimize) false detections when the intra-burst data presents a long sequence of repeating data.

If, in operation S420, the OLT 100 determines that the convergence does not exceed the first threshold, the OLT 100 may determine that an upstream burst is not present in the parallel data, and, thus, the parallel data contains random noise. Therefore, the OLT 100 may proceed back to operation S410 and continue to monitor incoming data in chunks for a convergence event. If, in operation S420, the OLT 100 determines that the convergence does exceed the first threshold, the OLT 100 may proceed to operation S430.

In operation S430, the OLT 100 may determine whether the number of consecutive words in the chunk exceeds a second threshold. For example, the OLT 100 may determine whether the number of 32 bit words in the chunk exceeds the second threshold. The second threshold may be empirically determined. For example, the second threshold may be calculated based on a characterization of the intra-burst data to reduce (or, alternatively, minimize) false detections when the infra-burst data presents a long sequence of repeating data.

If, in operation S430, the OLT 100 determines that the number of words does not exceed the second threshold, the OLT 100 may determine that an upstream burst is not present in the parallel data, and proceed back to operation S410 to continue to monitor incoming data in chunks for the convergence event. If in operation S430, the OLT 100 determines that the number of words exceeds the second threshold, the OLT 100 may proceed to operation S440.

In operation S440, the OLT 100 may assert a positive indication of the convergence event, if the OUT 100 determines that the number of words exceeds the second threshold, and thus, a valid optical signal is present in the parallel data. In some example embodiments, the valid optical signal may be a preamble, however, example embodiments are not limited thereto.

Thereafter, as discussed above with reference to FIG. 3, in operation S500, the OLT 100 may selectively assert a receiver reset in response to the OLT 100 detecting the convergence event. The receiver reset signal may activate any number of other operations to place the processing circuitry 140 in a proper state to recover the payload data. The receiver reset may activate an optics reset, a CDR reset, or a SERDES reset. Therefore, the OLT 100 may perform a virtual signal detect based on detection of the convergence event by monitoring the incoming data itself, which includes using a portion of the upstream burst packet that is normally discarded due to amplifier gain mismatch (settling time) and due to the data not yet being aligned with the receiver clock (lock tune).

Thus, the OLT 100 may perform relatively fast optical signal detection that is scalable with increasing data rates. By performing the virtual signal detect, the our 100 may allow for shorter preambles, thus, leading to more efficient bandwidth utilization than a conventional optical signal detect.

In other example embodiments, the OLT 100 may detect whether the ONU 200 associated with the upstream burst is rouge based on the detection of the convergence event For example, if the laser for ONU 200 is stuck on it will transmit data in a timeslot assigned to other ONUs. To detect this fault, the OLT 100 looks for a convergence event during an unassigned timeslot. If a convergence event is detected, the OLT 100 may determine that the ONU 200 is a rogue ONU, and, for example, may generate an alert.

FIG. 6 illustrates an upstream signal received by an optical line terminal from an optical network terminal according to example embodiments.

Referring to FIG. 6, the beginning of a burst may contain a preamble, typically a repeating logical '10' pattern used to align the receiver of the OLT 100 to the data before actual data is present.

Subsequent to the preamble, a delimiter may be present. The delimiter may be a desired (or, alternatively a predetermined) bit pattern that separates the preamble and packet data.

The packet data may include header information, payload data and a trailer. The header information may be data for higher level management of the packet data, the payload data may be the actual data being transported through the system, and the trailer may contain parity information for detection of bit errors within the burst.

As discussed above, the OLT 100 may perform a virtual signal detect to detect the start of an upstream burst, typically represented by a preamble, based on detection of a convergence event in an upstream burst prior to the data being aligned with the receiver clock (lock time). Therefore, the OLT 100 may perform relatively fast optical signal detection that is scalable with increasing data rates. By performing the virtual signal detect, the OLT 100 may allow for shorter preambles, thus, leading to more efficient bandwidth utilization than a conventional optical signal detect.

Example embodiments being thus described, it will be obvious that the same may be varied in many ways. Such variations are not to be regarded as a departure from the spirit and scope of example embodiments, and all such modifications as would be obvious to one skilled in the art are intended to be included within the scope of the claims.

Although the terms first, second, etc. may be used herein to describe various elements, these elements should not be limited by these terms. These terms are only used to distinguish one element from another. For example, a first element could be termed a second element, and similarly, a second element could be termed a first element, without departing from the scope of this disclosure. As used herein, the term "and/or," includes any and all combinations of one or more of the associated listed items.

When an element is referred to as being "connected," or "coupled," to another element, it can be directly connected or coupled to the other element or intervening elements may be present. By contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular example embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Specific details are provided in the description to provide a thorough understanding of example embodiments. However, it will be understood by one of ordinary skill in the art that example embodiments may be practiced without these specific details. For example, systems may be shown in block diagrams so as not to obscure the example embodiments in unnecessary detail. In other instances, well-known processes, structures and techniques may be shown without unnecessary detail in order to avoid obscuring example embodiments.

As discussed herein, illustrative embodiments are described with reference to acts and symbolic representations of operations (e.g., in the form of flow charts, flow diagrams, data flow diagrams, structure diagrams, block diagrams, etc.) that may be implemented as program modules or functional processes include routines, programs, objects, components, data structures, etc., that perform particular tasks or implement particular abstract data types and may be implemented using existing hardware at, for example, existing endpoints, clients, gateways, nodes, agents, controllers, computers, cloud based servers, web servers, proxies or proxy servers, application servers, and the like. As discussed later, such existing hardware may include, inter alia, one or more Central Processing Units (CPUs), system-on-chip (SOC) devices, digital signal processors (DSPs), application-specific-integrated-circuits, field programmable gate arrays (FPGAs) computers or the like.

Although a flow chart or communication flow diagram may describe the operations as a sequential process, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "storage medium", "computer readable storage medium" or "non-transitory computer readable storage medium" may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, example embodiments may be implemented by hardware, software, firmware, middleware, microcode, hardware description languages, or any combination thereof. When implemented in software, firmware, middle a e or microcode, the program code or code segments to perform the necessary tasks may be stored in a machine or computer readable medium such as a computer readable storage medium. When implemented in software, a processor or processors will perform the necessary tasks.

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

The terms "including" and/or "having", as used herein, are defined as comprising (i.e., open language). The term "coupled", as used herein, is defined as connected, although not necessarily directly, and not necessarily mechanically. Terminology derived from the word "indicating" (e.g., "indicates" and "indication") is intended to encompass all the various techniques available for communicating or referencing the object/information being indicated. Some, but not all, examples of techniques available for communicating or referencing the object/information being indicated include the conveyance of the object/information being indicated, the conveyance of an identifier of the object/information being indicated, the conveyance of information used to generate the object/information being indicated, the conveyance of some part or portion of the object/information being indicated, the conveyance of some derivation of the object/information being indicated, and the conveyance of some symbol representing the object/information being indicated.

According to example embodiments, clients, gateways, nodes, agents controllers, computers, cloud based servers, web servers, application servers, proxies or proxy servers, and the like, may be (or include) hardware, firmware, hardware executing software or any combination thereof. Such hardware may include one or more Central Processing Units (CPUs), system-on-chip (SOC) devices, digital signal processors (DSPs), application-specific-integrated-circuits (ASICs), field programmable gate arrays (FPGAs) computers or the like configured as special purpose machines to perform the functions described herein as well as any other well-known functions of these elements. In at least some cases, CPUs, SOCs, DSPs, ASICs and FPGAs may generally be referred to as processing circuits, processors and/or microprocessors.

The endpoints, clients, gateways, nodes, agents, controllers, computers, cloud based servers, web servers, application servers, proxies or proxy servers, and the like, may also include various interfaces including one or more transmitters/receivers connected to one or more antennas, a computer readable medium, and (optionally) a display device. The one or more interfaces may be configured to transmit/receive (wireline and/or wirelessly) data or control signals via respective data and control planes or interfaces to/from one or more network elements, such as switches, gateways, termination nodes, controllers, servers, clients, and the like.

Benefits, other advantages, and solutions to problems have been described above with regard to specific embodiments of the invention. However, the benefits, advantages, solutions to problems, and any element(s) that may cause or result in such benefits, advantages, or solutions, or cause such benefits, advantages, or solutions to become more pronounced are not to be construed as a critical, required, or essential feature or element of any or all the claims.

The example embodiments may have different forms and be combined, and should not be construed as being limited to the descriptions set forth herein.

We claim:

1. An optical line terminal (OLT) comprising:
   processing circuitry configured to,
   monitor a digital signal for a convergence event, the digital signal representing an optical signal received from an optical network terminal (ONT), the convergence event being an event associated with the ONT, the processing circuitry configured to monitor the digital signal for the convergence event by one of (i) detecting a level of randomness in a word included in the digital signal based on at least the digital signal, a delayed version of the digital signal and a first threshold and (ii) detecting a level of disparity of the digital signal based on at least a sum of the word included in the digital signal and a second threshold,
   reset one or more components of the processing circuitry in response to detection of the convergence event, and
   process, via the one or more components, an upstream burst of data associated with the digital signal after resetting the one or more components.

2. The OLT of claim 1, wherein the processing circuitry comprises:
   a clock data recover (CDR) circuit configured to perform a lock operation to align a phase of the digital signal with a reference clock associated with the OLT, and
   a virtual signal detector configured to detect the convergence event prior to completion of the lock operation.

3. The OLT of claim 1, wherein the OLT further comprises:
   an optical module configured to,
   receive the optical signal, the optical module including at least an optical receiver having a detection threshold associated therewith, the OLT configured to adjust, during a settling time, the detection threshold based on the optical signal, and wherein
   the processing circuitry is configured to detect the convergence event prior to an expiration of the settling time.

4. The OLT of claim 1, wherein the processing circuitry is configured to monitor the digital signal in one of discrete chunks of data and a moving average of the data.

5. The OLT of claim 4, wherein the discrete chucks of data are each 32 bits.

6. The OLT of claim 4, wherein the processing circuitry further comprises:
   a serial/deserializer configured to convert the data within the digital signal from serial data to parallel data.

7. The OLT of claim 1, wherein the processing circuitry is configured to one of (i) separate random intra-burst data from signal data and (ii) detect whether the ONT is rouge based on detection of the convergence event.

8. The OLT of claim 7, wherein the signal data is a preamble of the upstream burst from the ONT.

9. A method of operating an optical line terminal (OLT), the method comprising:
 monitoring a digital signal for a convergence event, the digital signal representing an optical signal received from an optical network terminal (ONT), the convergence event being an event associated with the ONT, the monitoring including one of (i) detecting a level of randomness in a word included in the digital signal based on at least the digital signal, a delayed version of the digital signal and a first threshold and (ii) detecting a level of disparity of the digital signal based on at least a sum of the word included in the digital signal and a second threshold;
 resetting one or more components in response to detection of the convergence event; and
 processing, via the one or more components, an upstream burst of data associated with the digital signal after resetting the one or more components.

10. The method of claim 9, wherein the monitoring comprises:
 performing, via a clock data recover (CDR) circuit, a lock operation to align a phase of the digital signal with a reference clock associated with the OLT, and
 detecting, via a virtual signal detector, the convergence event prior to completion of the lock operation.

11. The method of claim 9, further comprising:
 receiving, via an optical module, the optical signal, the optical module including at least an optical receiver having a detection threshold associated therewith, the OLT configured to adjust, during a settling time, the detection threshold based on the optical signal, and wherein
 the monitoring detects the convergence event prior to an expiration of the settling time.

12. The method of claim 9, wherein the monitoring monitors the digital signal in one of discrete chunks of data and a moving average of the data.

13. The method of claim 9, wherein the monitoring monitors the digital signal for the convergence event by detecting one of (i) a level of randomness in the digital signal and (ii) a level of disparity of the digital signal.

14. A non-transitory computer readable medium storing instructions that, when executed by processing circuitry associated with an optical line terminal (OLT), configures the processing circuitry to,
 monitor a digital signal for a convergence event, the digital signal representing an optical signal received from an optical network terminal (ONT), the convergence event being an event associated with the ONT, the processing circuitry configured to monitor the digital signal for the convergence event by one of (i) detecting a level of randomness in a word included in the digital signal based on at least the digital signal, a delayed version of the digital signal and a first threshold and (ii) detecting a level of disparity of the digital signal based on at least a sum of the word included in the digital signal and a second threshold,
 reset one or more components of the processing circuitry in response to detection of the convergence event, and
 process, via the one or more components, an upstream burst of data associated with the digital signal after resetting the one or more components.

15. The non-transitory computer readable medium of claim 14, wherein the instructions, when executed, configure the processing circuitry to,
 perform, via a clock data recover (CDR) circuit, a lock operation to align a phase of the digital signal with a reference clock associated with the OLT, and
 detect, via a virtual signal detector, the convergence event prior to completion of the lock operation.

16. The non-transitory computer readable medium of claim 14, wherein the instructions, when executed, configure the processing circuitry to,
 receive, via an optical module, the optical signal, the optical module including at least an optical receiver having a detection threshold associated therewith, the OLT configured to adjust, during a settling time, the detection threshold based on the optical signal, and wherein
 the processing circuitry is configured to detect the convergence event prior to an expiration of the settling time.

17. The non-transitory computer readable medium of claim 14, wherein the instructions, when executed, configure the processing circuitry to,
 monitor the digital signal for the convergence event by detecting one of (i) a level of randomness in the digital signal and (ii) a level of disparity of the digital signal.

* * * * *